United States Patent
Morozumi et al.

(10) Patent No.: US 12,379,382 B2
(45) Date of Patent: Aug. 5, 2025

(54) ANALYSIS METHOD, ANALYTICAL METHOD AND MICROORGANISM IDENTIFICATION METHOD

(71) Applicants: KEIO UNIVERSITY, Tokyo (JP); SHIMADZU CORPORATION, Kyoto (JP)

(72) Inventors: Miyuki Morozumi, Tokyo (JP); Megumi Sakuma, Tokyo (JP); Koretsugu Ogata, Kyoto (JP); Keisuke Shima, Kyoto (JP); Shinji Funatsu, Kyoto (JP)

(73) Assignees: KEIO UNIVERSITY, Tokyo (JP); SHIMADZU CORPORATION, Kyoto (JP)

( * ) Notice: Subject to any disclaimer, the term of this patent is extended or adjusted under 35 U.S.C. 154(b) by 1095 days.

(21) Appl. No.: 17/280,302

(22) PCT Filed: Sep. 18, 2019

(86) PCT No.: PCT/JP2019/036594
§ 371 (c)(1),
(2) Date: Mar. 26, 2021

(87) PCT Pub. No.: WO2020/066795
PCT Pub. Date: Apr. 2, 2020

(65) Prior Publication Data
US 2022/0034900 A1    Feb. 3, 2022

(30) Foreign Application Priority Data
Sep. 28, 2018    (JP) ................. 2018-185630

(51) Int. Cl.
*G01N 33/68*    (2006.01)
*C12Q 1/14*    (2006.01)

(52) U.S. Cl.
CPC .......... *G01N 33/6848* (2013.01); *C12Q 1/14* (2013.01)

(58) Field of Classification Search
CPC ......... G01N 33/6848; G01N 33/56938; G01N 33/6851; C12Q 1/14
See application file for complete search history.

(56) References Cited

PUBLICATIONS

Spinali, Sébastien, et al. "Microbial typing by matrix-assisted laser desorption ionization-time of flight mass spectrometry: do we need guidance for data interpretation?." Journal of clinical microbiology 53.3 (2015): 760-765. (Year: 2015).*
Communication dated Sep. 23, 2023, issued in Chinese Application No. 201980062766.3.
Hai Liu et al., "Genotyping research on M protein gene in GAS from children in Mentougou, Beijing", Chin J Health Lab Tec, Nov. 2015, vol. 25, No. 22, pp. 3911-3912, and p. 3923 (8 pages).
(Continued)

*Primary Examiner* — Jill A Warden
(74) *Attorney, Agent, or Firm* — Sughrue Mion, PLLC

(57) ABSTRACT

An analysis method includes: acquiring data corresponding to a mass spectrum obtained by subjecting a sample containing a microorganism to mass spectrometry; and acquiring information on Group A *Streptococcus* of emm type 1, based on the presence or absence, or magnitude of a peak in a first range of m/z of 10930 or more to 10945 or less in the mass spectrum.

4 Claims, 13 Drawing Sheets

(56) References Cited

PUBLICATIONS

Hercules Moura et al., "MALDI-TOF mass spectrometry as a tool for differentiation of invasive and noninvasive *Streptococcus pyogenes* isolates", FEMS Immunology & Medical Microbiology, Blackwell Publishing, 2008, pp. 333-342, vol. 53, Issue 3.

Megumi Sakuma et al., "Evaluation of the ability of MALDI-TOF MS to discriminate group A hemolytic streptococci from emm1 strains", Programs and Abstracts of Joint Society of 67th Annual Meeting of Eastern Japan Society of 67th Annual Meeting of Eastern Japan Branch of the Japanese Association for Infectious Diseases and the 65th Annual Meeting of East Japan Branch Meeting of the Japanese Society of Chemotherapy, Oct. 2018, p. 163, 112.

"Emm 1 strain identification of group A hemolytic streptococci using MALDI-TOF MS and statistical analysis software eMSTAT Solution™", MALDI-TOF mass spectrometry, Application News, No. B91, Shimadzu Corporation, Jan. 2019, 4 pages.

"Establishment of surveillance for severe streptococcal and pneumococcal infections, analysis of their etiology, and research on their diagnosis and treatment (H 22—Emerging—General—013)", Health and Labour Sciences Research Grants "Research on emerging and re-emerging infectious diseases such as new strains of influenza", 2010, 4 pages.

Written Opinion for PCT/JP2019/036594, dated Dec. 3, 2019.

International Search Report for PCT/JP2019/036594, dated Dec. 3, 2019.

Office Action dated Feb. 8, 2022 issued by the Japanese Patent Office in Japanese 2020-548559.

Office Action issued Jun. 27, 2024 in Chinese Application No. 201980062766.3.

Zhang Haomin, et al., "Application of MALDI-TOF MS in the identification and typing of *Streptococcus pyogenes*", Medical Society of Chinese Walis, Twelfth National Annual Society of Clinical Microbiology and Infectious Society, 2015, p. 64 (2 pages total).

Guo Ling, et al., "Matrix-assisted laser desorption/ionization time-of-flight mass spectrometry in clinical microbial detection", Clinical Laboratory Journal (Electronic Edition), Jun. 2012, vol. 1, No. 2, pp. 111-113 (11 pages total).

Communication dated Sep. 14, 2024, from the Chinese Patent Office in Application No. 201980062766.3.

\* cited by examiner

ANALYSIS METHOD, ANALYTICAL METHOD AND MICROORGANISM IDENTIFICATION METHOD

CROSS REFERENCE TO RELATED APPLICATIONS

This application is a National Stage of International Application No. PCT/JP2019/036594 filed Sep. 18, 2019, claiming priority based on Japanese Patent Application No. 2018-185630 filed Sep. 28, 2018.

TECHNICAL FIELD

The present invention relates to an analysis method, an analytical method and a microorganism identification method.

BACKGROUND ART

Group A *Streptococcus* (GAS) is a Gram-positive coccus that causes various symptoms in infected individuals. GAS causes pharyngitis, tonsillitis, and other symptoms, and invades blood and tissues, causing invasive GAS infections. An invasive GAS infection associated with shock is called Streptococcal toxic shock syndrome (STSS). STSS progresses rapidly after initial symptoms such as pain in the extremities and fever, causing necrosis of tissues, multiple organ failures, and the like, which can lead to the death of the infected individuals in a short period of time such as several tens of hours.

GAS is classified into 130 or more of serotypes and M types according to the antigenicity of the M proteins on the surfaces of the bacterial cells. The classification by the emm types based on the sequence from the 5' terminal of the emm gene that encodes the M protein, instead of the M types, has been recently used, and 234 emm types have been registered. For the cases of STSS, the emm1 type has been detected in many cases, and the emm type 12 has also been detected with less frequency than the emm1 type. Identification of GAS types is important to appropriately treat and accurately analyze GAS infections.

The emm type has been identified by sequencing the DNA sequence of the emm gene of GAS. However, this involves a problem of amount of time required for amplification of DNA by PCR, for example. NPTL1 describes identification of invasive GAS collected from a subject with necrotizing fasciitis and noninvasive GAS collected from a subject with pharyngitis, using mass spectrometry that does not require PCR or the like.

CITATION LIST

Non-Patent Literature

NPTL1: Moura H, Woolfitt A R, Carvalho M G, Pavlopoulos A, Teixeira L M, Satten G A, Barr J R. "MALDI-TOF mass spectrometry as a tool for differentiation of invasive and noninvasive *Streptococcus pyogenes* isolates" FEMS Immunology & Medical Microbiology, (the United States), Blackwell Publishing, Aug. 1, 2008, Volume 53, Issue 3, pp. 333-342

SUMMARY OF INVENTION

Technical Problem

The method of NPTL 1 cannot identify an emm type. Identification of the emm type enables diagnosis, analysis or the like using information obtained from the emm type.

Solution to Problem

According to the 1st aspect of the present invention, an analysis method comprises: acquiring data corresponding to a mass spectrum obtained by subjecting a sample containing a microorganism to mass spectrometry; and acquiring information on Group A *Streptococcus* of emm type 1, based on the presence or absence, or magnitude of a peak in a first range of m/z of 10930 or more to 10945 or less in the mass spectrum.

According to the 2nd aspect of the present invention, an analytical method comprises: generating data corresponding to a mass spectrum obtained by subjecting a sample containing a microorganism to mass spectrometry; and acquiring information on Group A *Streptococcus* of emm type 1 by the analysis method according to the 1st aspect.

According to the 3rd aspect of the present invention, in the analytical method according to the 2nd aspect, it is preferred that, in the mass spectrometry, the sample is ionized by matrix-assisted laser desorption/ionization, using sinapic acid or CHCA as a matrix.

According to the 4th aspect of the present invention, a microorganism identification method comprises: analyzing a microorganism by the analytical method according to the 2nd or 3rd aspect; and identifying whether or not the microorganism is Group A *Streptococcus* of emm type 1, based on the presence or absence, or magnitude of a peak in the first range.

According to the 5th aspect of the present invention, it is preferred that the analysis method according to the 1st aspect further comprises: acquiring information on Group A *Streptococcus* of emm type 12, based on the presence or absence, or magnitude of a peak in a second range of m/z of 6908 or more to 6918 or less in the mass spectrum.

According to the 6th aspect of the present invention, an analytical method comprises: generating data corresponding to a mass spectrum obtained by subjecting a sample containing a microorganism to mass spectrometry; and acquiring information on Group A *Streptococcus* of emm type 12 by the analysis method according to the 5th aspect.

According to the 7th aspect of the present invention, in the analytical method according to the 6th aspect, it is preferred that, in the mass spectrometry, the sample is ionized by matrix-assisted laser desorption/ionization, using sinapic acid or CHCA as a matrix.

According to the 8th aspect of the present invention, a microorganism identification method comprises: analyzing a microorganism by the analytical method according to the 6th or 7th aspect; and identifying whether or not the microorganism is Group A *Streptococcus* of emm type 12, based on the presence or absence, or magnitude of a peak in the second range.

Advantageous Effects of Invention

The present invention enables identification of an emm type of a microorganism, such as whether a microorganism is of emm1 type or emm type 12, by mass spectrometry.

DESCRIPTION OF EMBODIMENT

Figure 1:
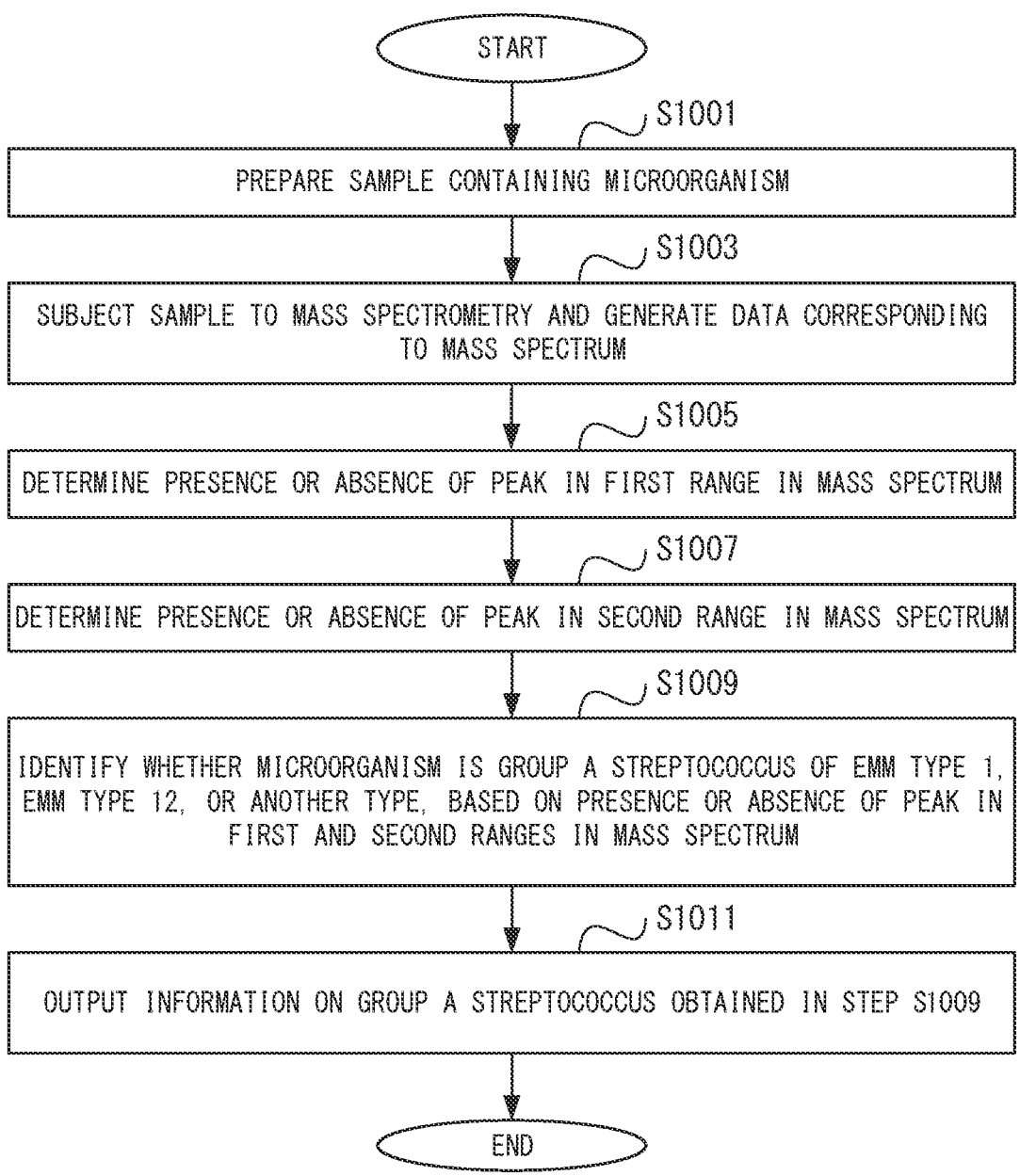
FIG. 1 is a flowchart illustrating flow of an analytical method according to a first embodiment.

Embodiments of the present invention will be described below with reference to the drawings.

First Embodiment

An analytical method according to the present embodiment is to obtain information on emm type, based on the presence or absence of a peak in the predetermined m/z range in a mass spectrum obtained by mass spectrometry of a sample containing a microorganism.

Sample

The sample is not particularly limited as long as being a sample containing Group A *Streptococcus* (GAS) or a microorganism which may be GAS. The sample is collected preferably from an animal such as a human. The sample collected from a human can be any body fluid that can contain GAS, such as a fluid adhering to the pharynx or tonsil, or an exudate from the wound of the skin, blood, a cerebrospinal fluid, and urine. For example, in an inspection to identify GAS with which a subject is infected, it is preferred that blood be collected as a sample from the subject who is a person to be inspected, or a pharynx swab be collected as a sample by swabbing the pharynx of the person to be inspected with a cotton swab. Since GAS can also be present in a healthy human, the person to be inspected is not particularly limited to the subject infected with GAS.

The collected sample containing microorganisms undergoes isolation culture. The isolation culture is performed by applying the sample on a blood agar culture medium containing 5% defibrinated blood of sheep, and then culturing the sample at 37° C. in 5% carbon dioxide gas. After 24 hours, a colony suspected of having GAS is identified based on zones of hemolysis and the like of colonies grown on the medium. For example, the majority of GAS exhibit β hemolysis after 24 hours of culturing. Serum grouping may be performed on the colonies using an appropriate grouping kit or the like. A mass spectrometry sample is prepared from the colony having GAS. The mass spectrometry sample may also be prepared by using a colony obtained by further culturing in a liquid culture medium.

Numerical values of the composition of the medium, the culturing temperature, the culturing time, and other conditions can be adjusted, as appropriate, How to prepare the mass spectrometry sample is not particularly limited. For mass spectrometry using matrix-assisted laser desorption/ionization (hereinafter referred to as MALDI), a colony obtained by culturing is collected, a solution containing a matrix (hereinafter referred to as a matrix solution) is added to the resultant sample, which is then added dropwise on a MALDI sample plate and dried. The matrix solution may be added after placing the sample on the MALDI sample plate. Although the kind of the matrix is not particularly limited, the kind of the matrix is preferably sinapic acid or α-cyano-4-hydroxycinnamic acid (CHCA) from the viewpoint of accurately performing mass spectrometry, more preferably sinapic acid from the viewpoint of accurately detecting molecules with high mass such as a dozen kDa or more. As a solvent for the matrix solution, a solvent obtained by adding 0 vol % to 3 vol % trifluoroacetic acid (TFA) to a solution containing several tens of percentages by volume of an organic solvent such as acetonitrile in water may be used.

The mass spectrometry sample may be prepared by extracting a protein from a microorganism contained in the obtained colony, and then adding the matrix solution to the resultant extract.

Mass Spectrometry

As a method for ionization in mass spectrometry, MALDI is preferred for easily producing monovalent ions and thus easily performing analysis. Time-of-flight mass spectrometry is preferred for detecting a high-mass molecule with several kDa or higher with high accuracy. Time-of-flight mass spectrometry using MALDI (hereinafter referred to as MALDI-TOFMS) is particularly preferred because of having both advantages of MALDI and time-of-flight mass spectrometry. However, the method of mass spectrometry is not particularly limited as long as a peak caused by a foreign substance does not appear in the m/z range in which a peak of GAS of emm type 1 or emm type 12 is to be detected. For example, any appropriate ionization method such as an electrospray method may be used. A mass analyzer such as a quadrupole mass filter or an ion trap may be used. A single mass spectrometer may be used. However, a plurality of appropriate mass analyzers may be used in combination to perform multi-stage mass spectrometry. In mass spectrometry, data corresponding to a mass spectrum (hereinafter referred to as measured mass spectrum) obtained by detecting an ionized sample (sample ion) is generated.

Analysis of Mass Spectrum

In the measured mass spectrum, whether or not a microorganism contained in a sample is of emm type 1 is identified based on the presence or absence of a peak (first peak) in an m/z range of 10930 or more, preferably 10934 or more to 10945 or less, preferably 10940 or less (hereinafter referred to as the first range). The first range is preferably narrow for reducing a possibility of erroneously detecting an undesired peaka such as a peak of a foreign substance. However, if a mass spectrometer to be used has low accuracy, a peak which has to be the first peak may appear out of the first range. Thus, the first range is set preferably not to be too narrow. If a first peak is detected, it can be identified that the microorganism contained in the sample is GAS of emm type 1. If no first peaks are detected, it can be identified that the microorganism contained in the sample is not GAS of emm type 1. The analytical method according to the present embodiment enables identification of emm type 1 from GAS of specifically emm type 1, emm type 12, emm type 28, and emm type 89, based on the presence or absence of a first peak.

If a peak detected in the first range is not sufficiently intense, it may be identified that the microorganism contained in the sample is not GAS of emm type 1. In other words, whether or not microorganism is of emm type 1 may be identified based on the magnitude of a peak in the first range.

In the measured mass spectrum, whether or not a microorganism contained in a sample is of emm type 12 is identified based on the presence or absence of a peak in an m/z range of 6908 or more, preferably 6910 or more to 6918 or less, preferably 6914 or less (hereinafter referred to as the second range). The second range is preferably narrow for reducing a possibility of erroneously detecting an undesired peak such as a peak of a foreign substance. However, if a mass spectrometer to be used has low accuracy, a target peak may be out of the second range. Thus, the second range is set preferably not to be too narrow. If a second peak is detected, it can be identified that the microorganism contained in the sample is GAS of emm type 12. If no second peaks are detected, it can be identified that the microorganism contained in the sample is not GAS of emm type 12. The analytical method according to the present embodiment enables identification of emm type 12 from GAS of specifically emm type 1, emm type 12, emm type 28, and emm type 89, based on the presence or absence of a second peak.

If a peak detected in the second range is not sufficiently intense, it may be identified that the microorganism contained in the sample is not GAS of emm type 12. In other words, whether or not a microorganism is of emm type 12 may be identified based on the magnitude of a peak in the second range.

If none of first and second peaks is detected in the measured mass spectrum, it is identified that microorganism contained in the sample is neither GAS of emm type 1 nor GAS of emm type 12.

If both of the first and second peaks are detected in the measured mass spectrum, it is difficult to identify the emm type from the mass spectrum. Thus, the identification may not be performed.

Even if a first peak is detected in the measured mass spectrum, the microorganism contained in the sample may not be determined as GAS of emm type 1 only by the detection, but it may be determined that the microorganism is highly probably GAS of emm type 1 by the detection of the first peak and the emm type of the microorganism may be identified with an additional inspection in combination. The same applies to identification of emm type 12 from the second peak.

The analysis method (data analysis method) of mass spectrum may be performed using an analysis device (data analysis device) such as an information processor such as a personal computer or a processor integral with the mass spectrometer, or by a human such as an analyst. For the use of the analysis device, data indicating the detection intensity of ions is input from a detector of the mass spectrometer to the analysis device, to generate data corresponding to a mass spectrum. Then, the presence or absence of the first and second peak in this mass spectrum is determined. Alternately, data corresponding to a mass spectrum is input to the analysis device, and then, the presence or absence of the first and second peak in this mass spectrum is determined. Information on whether the microorganism is GAS of emm type 1 or emm type 12, acquired based on this determination, is output through being displayed on a display device such as a liquid crystal monitor, for example.

For identification of a microorganism collected from a subject in a clinical examination, information on whether the microorganism contained in the sample is GAS of emm type 1 or emm type 12 is provided to a physician or other healthcare professionals, for example. The physician uses this information to diagnose or treat the subject, and the healthcare professionals share this information to understand the medical condition of the subject.

FIG. 1 is a flowchart illustrating flow of a microorganism identification method including an analytical method according to the present embodiment. In the step S1001, a sample containing a microorganism is prepared. After the step S1001 is completed, the step S1003 is started. In the step S1003, the sample is subjected to mass spectrometry, and data corresponding to a mass spectrum is generated. After the step S1003 is completed, the step S1005 is started.

The step S1005 determines the presence or absence of a peak in the first range in the mass spectrum. After the step S1005 is completed, the step S1007 is started. The step S1007 determines the presence or absence of a peak in the second range in the mass spectrum. After the step S1007 is completed, the step S1009 is started.

In the step S1009, whether the microorganism is GAS of emm type 1, emm type 12, or another type is identified based on the presence or absence of a peak in the first and second ranges in the mass spectrum. After the step S1009 is completed, the step S1011 is started. In the step S1011, information on GAS acquired in the step S1009 is output to a display device or the like. After the step S1011 is completed, the process is completed.

By the above embodiment, the following actions and effects can be obtained.

(1) The analysis method according to the present embodiment comprises: acquiring data corresponding to a mass spectrum obtained by subjecting a sample containing a microorganism to mass spectrometry; and acquiring information on GAS of emm type 1, based on the presence or absence, or magnitude of a peak in a first range of m/z of 10930 or more to 10945 or less in the mass spectrum. This allows information on emm type 1 to be acquired using data acquired by mass spectrometry without performing PCR and the like.

(2) The analytical method according to the present embodiment comprises: generating data corresponding to a mass spectrum obtained by subjecting a sample containing a microorganism to mass spectrometry; and acquiring information on GAS of emm type 1 by the above analysis method. This allows information on the emm type 1 to be acquired promptly by mass spectrometry.

(3) In the analytical method according to the present embodiment, in the mass spectrometry, the sample is ionized by MALDI, using sinapic acid or CHCA as a matrix. This allows a monovalent ion to be easily produced, and thus a mass spectrum which can be easily analyzed can be obtained.

(4) The microorganism identification method according to the present embodiment comprises: analyzing a microorganism by the above analytical method; and identifying whether or not the microorganism is GAS of emm type 1 based on the presence or absence, or magnitude of a peak in the first range. This allows identification of whether or not the microorganism is GAS of emm type 1 by mass spectrometry without performing PCR and the like.

(5) The analysis method according to the present embodiment comprises: acquiring information on GAS of emm type 12, based on the presence or absence, or magnitude of a peak in the second range of m/z of 6908 or more to 6918 or less in the mass spectrum. This allows information on emm type 12 to be acquired using data acquired by mass spectrometry without performing PCR and the like.

(6) The analytical method according to the present embodiment comprises: generating data corresponding to a mass spectrum obtained by subjecting a sample containing a microorganism to mass spectrometry; and acquiring information on GAS of emm type 12 by the above analysis method. This allows information on the emm type 12 to be acquired promptly by mass spectrometry.

(7) The microorganism identification method according to the present embodiment comprises: analyzing a microorganism by the above analytical method; and identifying whether or not the microorganism is GAS of emm type 12 based on the presence or absence, or magnitude of a peak in the second range. This allows identification of whether or not the microorganism is GAS of emm type 12 by mass spectrometry without performing PCR and the like.

The present invention is not limited by the contents of the above embodiment. Other aspects conceivable within the scope of the technical idea of the present invention are encompassed in the scope of the present invention.

EXAMPLE

The following shows an example according to the present embodiment, but the present invention is not limited by specific devices and the like in this Example.

Mass spectra of GAS of emm type 1, emm type 12, emm type 28, and emm type 89, which were used as samples, were obtained by MALDI-TOFMS using a AXIMA microorganism identification system (Shimadzu Corporation). Sinapic acid was used as a matrix, and time-of-flight mass spectrometry was performed in a linear mode.

Figure 2:
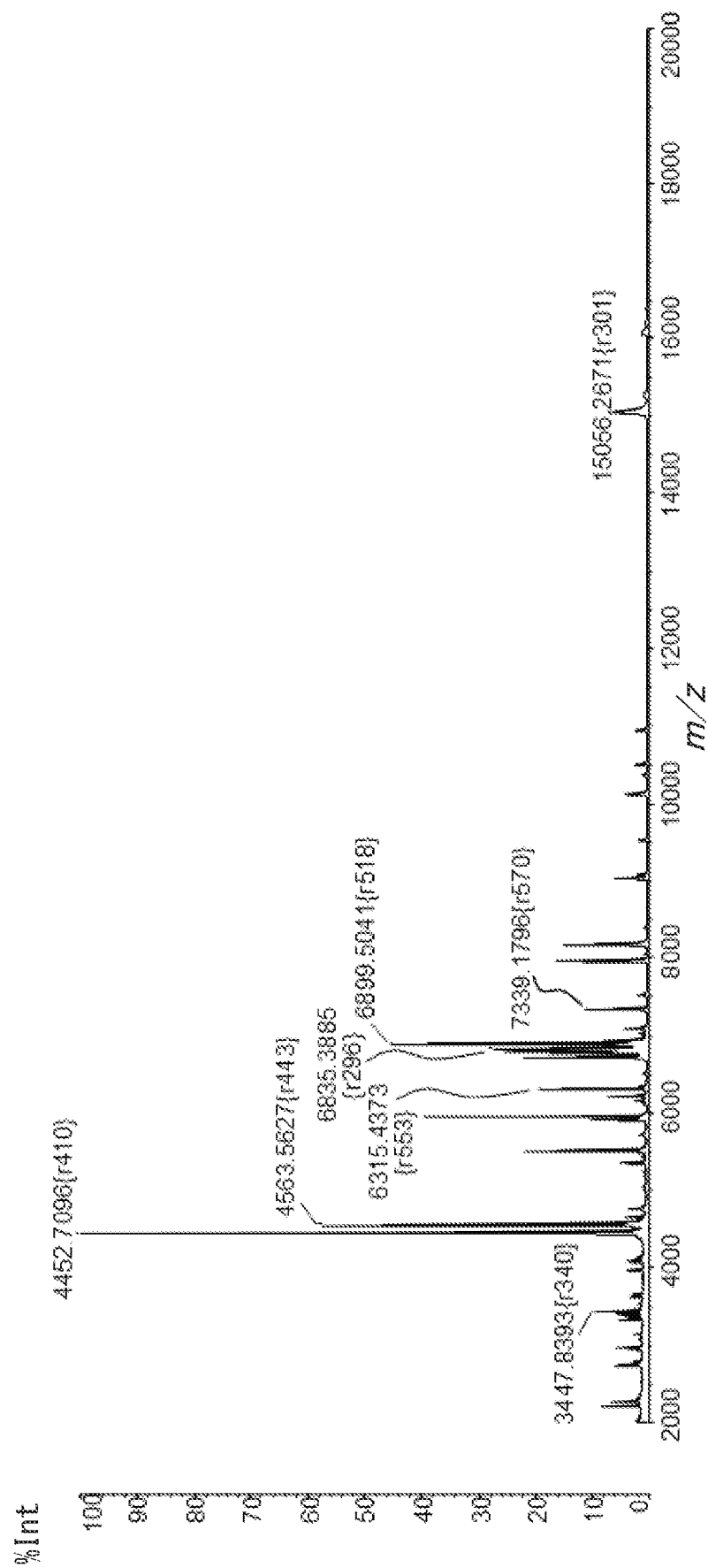
FIG. 2 is a mass spectrum in the m/z range of 2000 to 20000 obtained by mass spectrometry of microorganisms of emm type 1.
Figure 3:
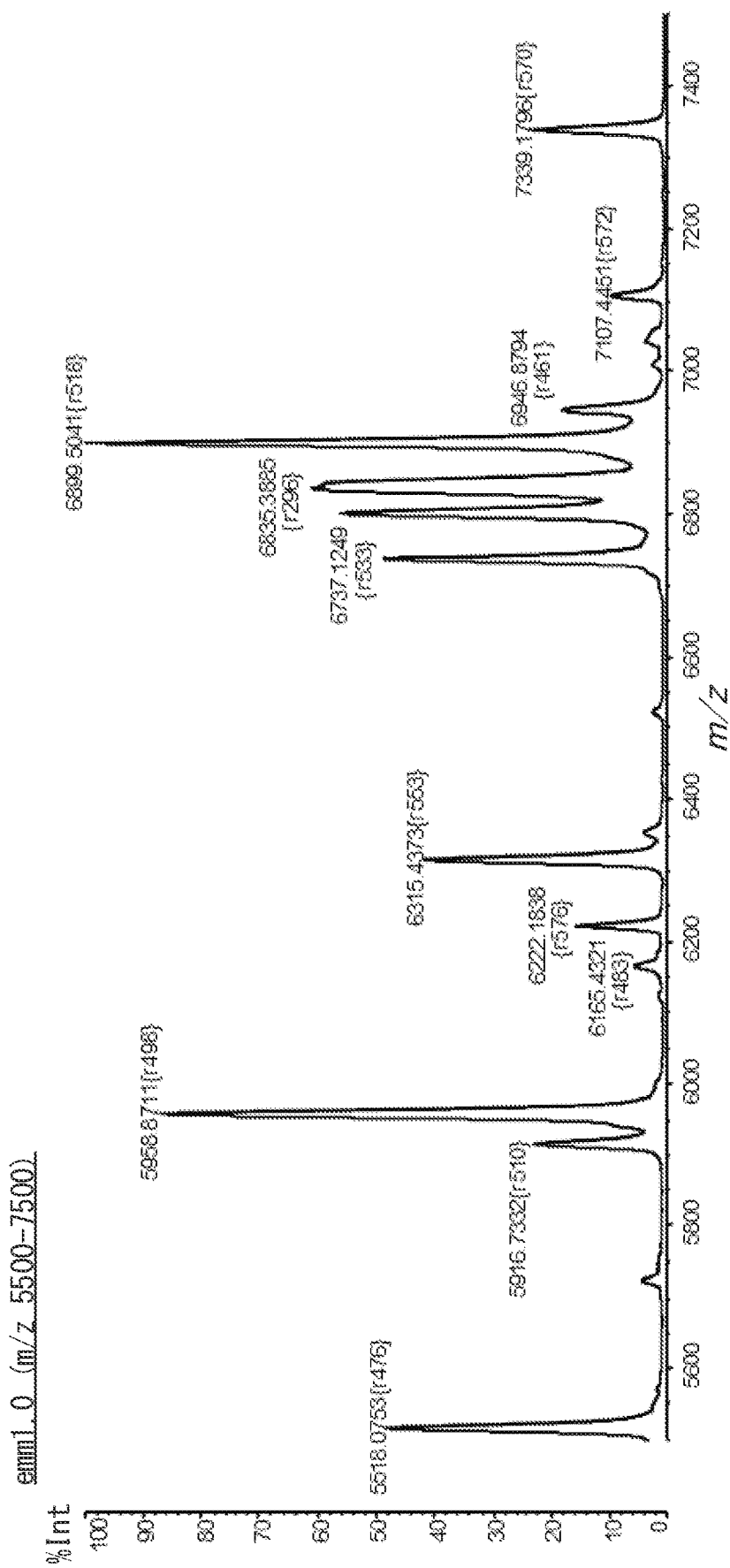
FIG. 3 is a mass spectrum in the m/z range of 5500 to 7500 obtained by mass spectrometry of microorganisms of emm type 1.
Figure 4:
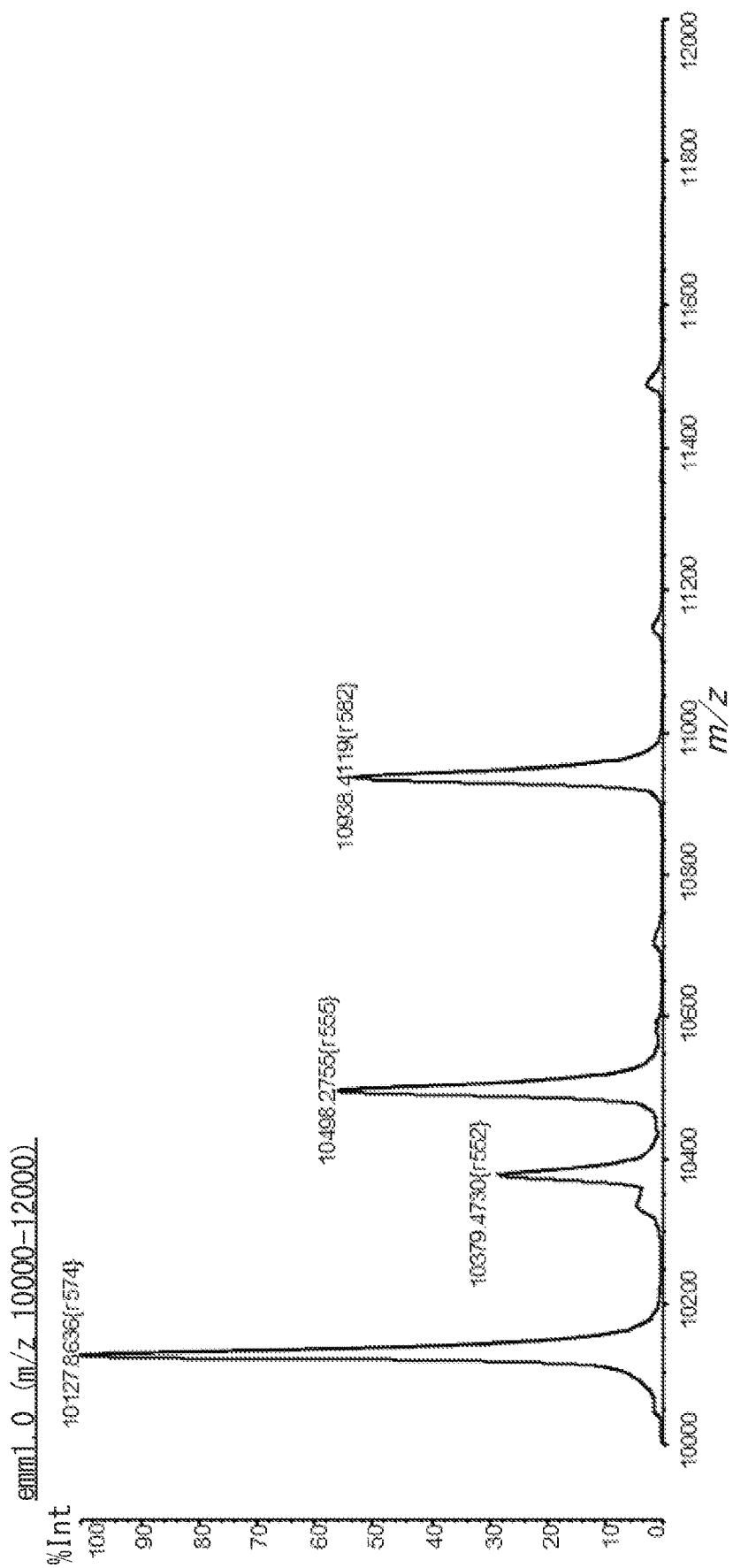
FIG. 4 is a mass spectrum in the m/z range of 10000 to 12000 obtained by mass spectrometry of microorganisms of emm type 1.

FIGS. 2, 3, and 4 are mass spectra of the sample prepared from microorganisms of emm type 1 (emm 1.0) in the m/z ranges of 2000 to 20000, 5500 to 7500, and 10000 to 12000, respectively. The numerical value indicated for each peak is m/z of the peak, and an ID identifying the peak is shown in parentheses. The same is also applied to the following figures.

Figure 5:
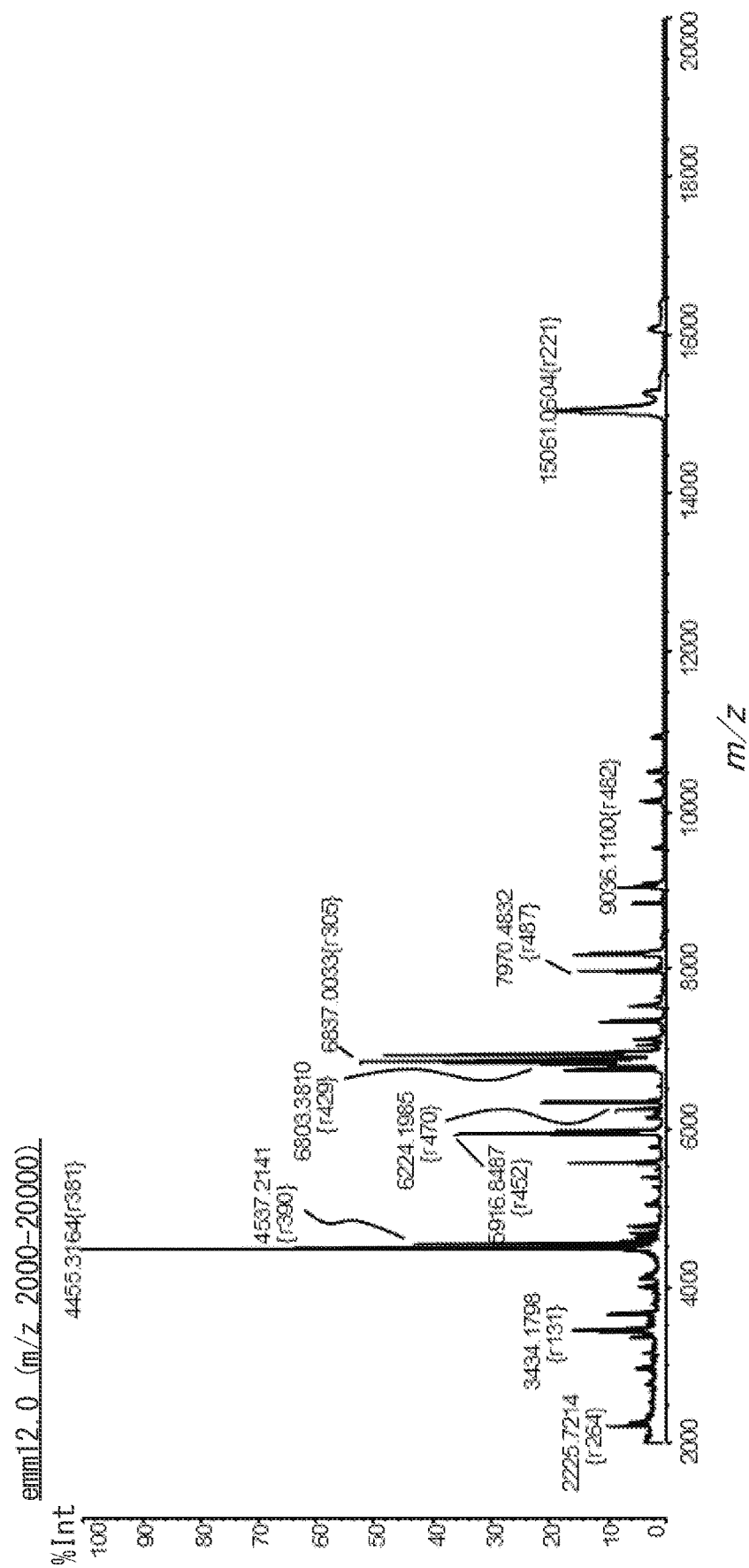
FIG. 5 is a mass spectrum in the m/z range of 2000 to 20000 obtained by mass spectrometry of microorganisms of emm type 12.
Figure 6:
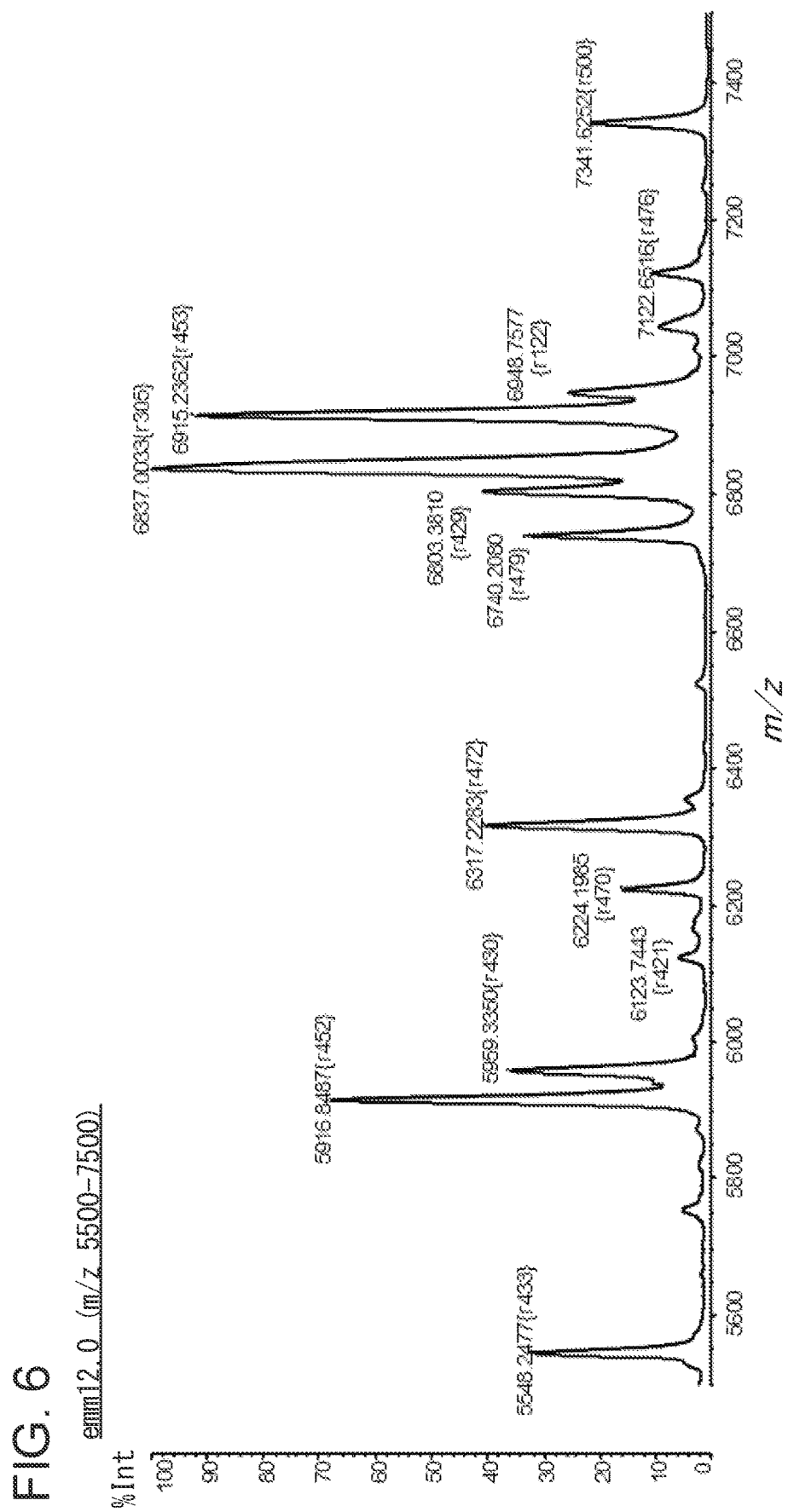
FIG. 6 is a mass spectrum in the m/z range of 5500 to 7500 obtained by mass spectrometry of microorganisms of emm type 12.
Figure 7:
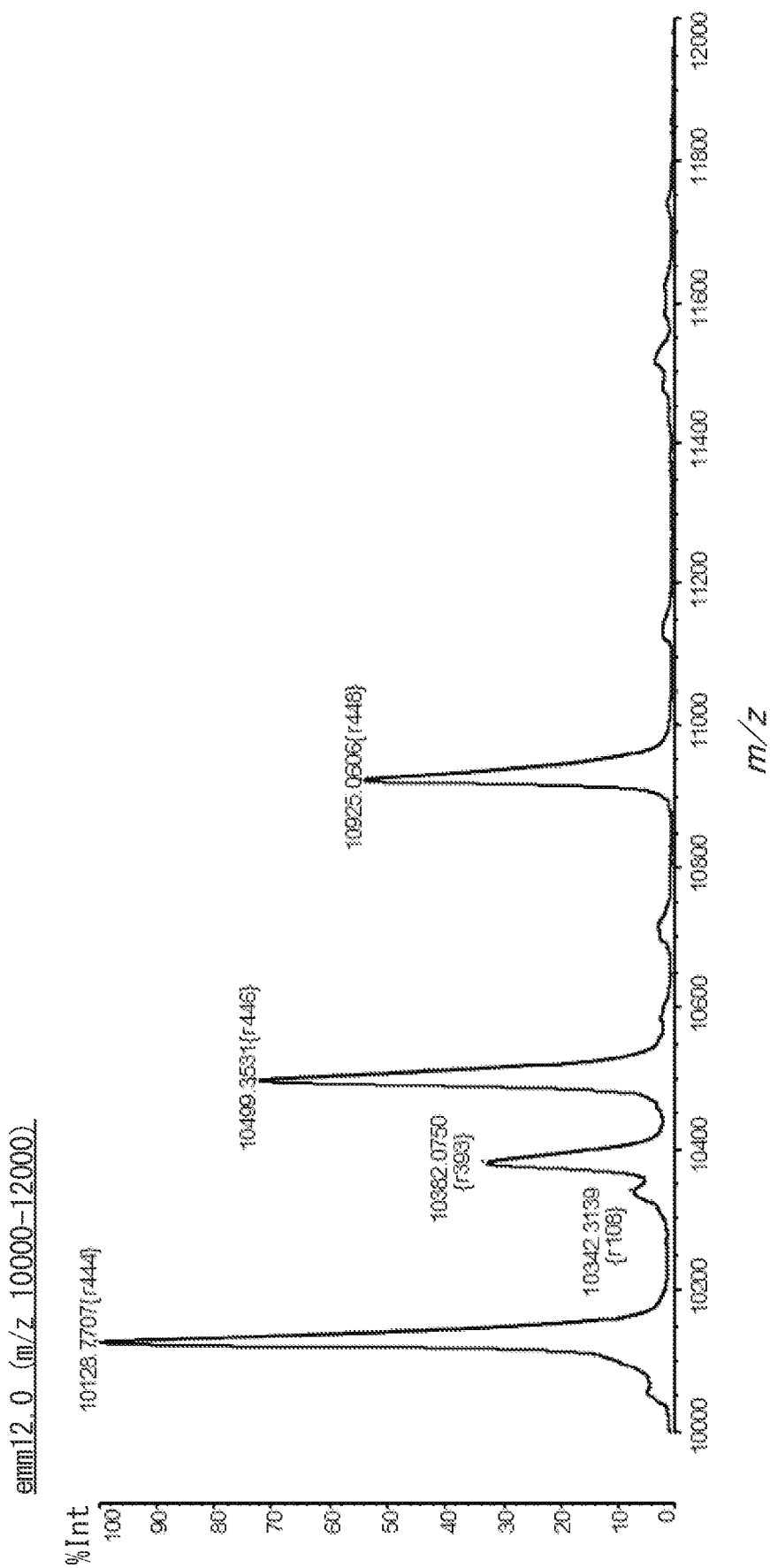
FIG. 7 is a mass spectrum in the m/z range of 10000 to 12000 obtained by mass spectrometry of microorganisms of emm type 12.

FIGS. 5, 6, and 7 are mass spectra of the sample prepared from microorganisms of emm type 12 (emm 12.0) in the m/z ranges of 2000 to 20000, 5500 to 7500, and 10000 to 12000, respectively.

Figure 8:
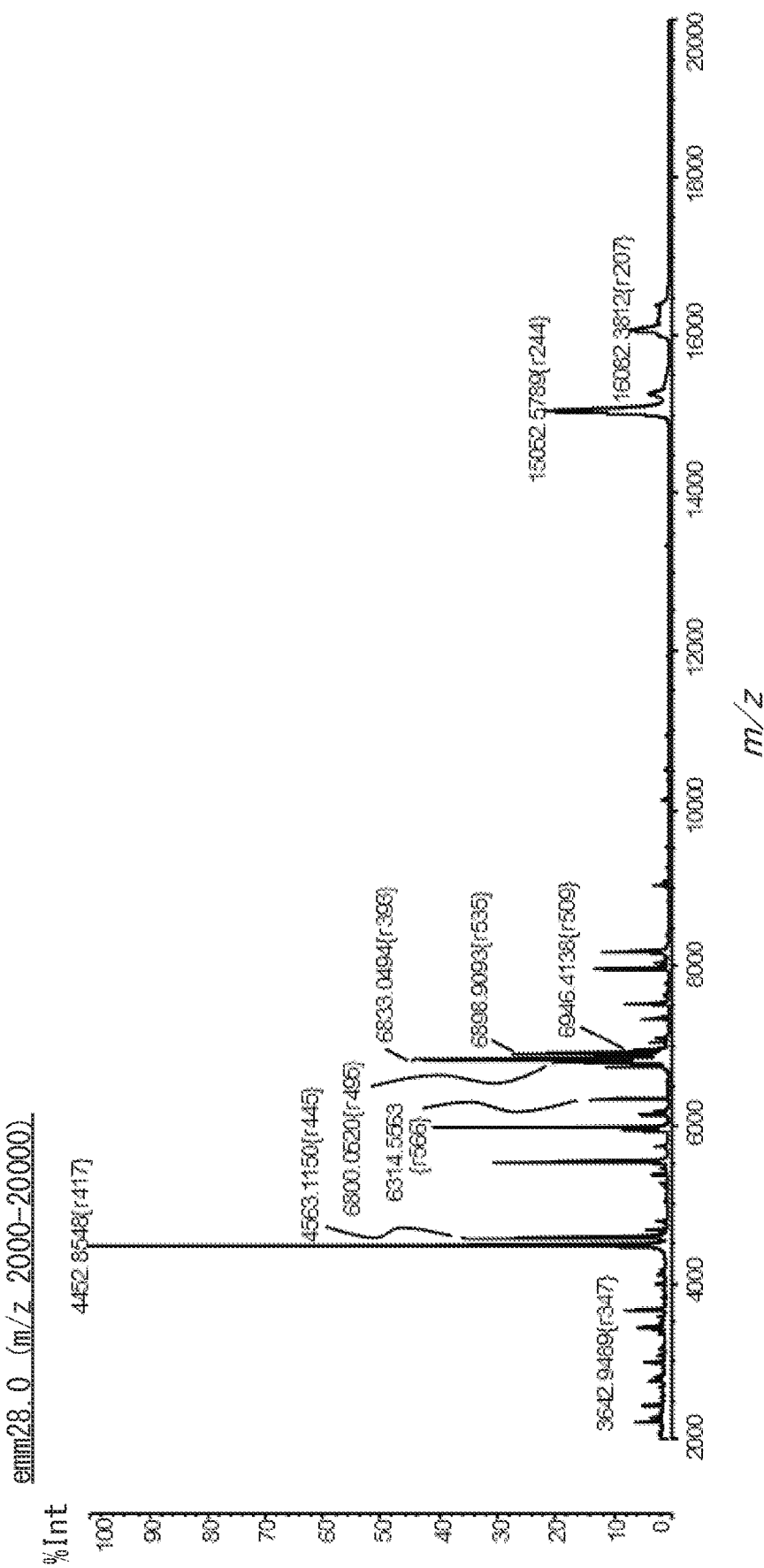
FIG. 8 is a mass spectrum in the m/z range of 2000 to 20000 obtained by mass spectrometry of microorganisms of emm type 28.
Figure 9:
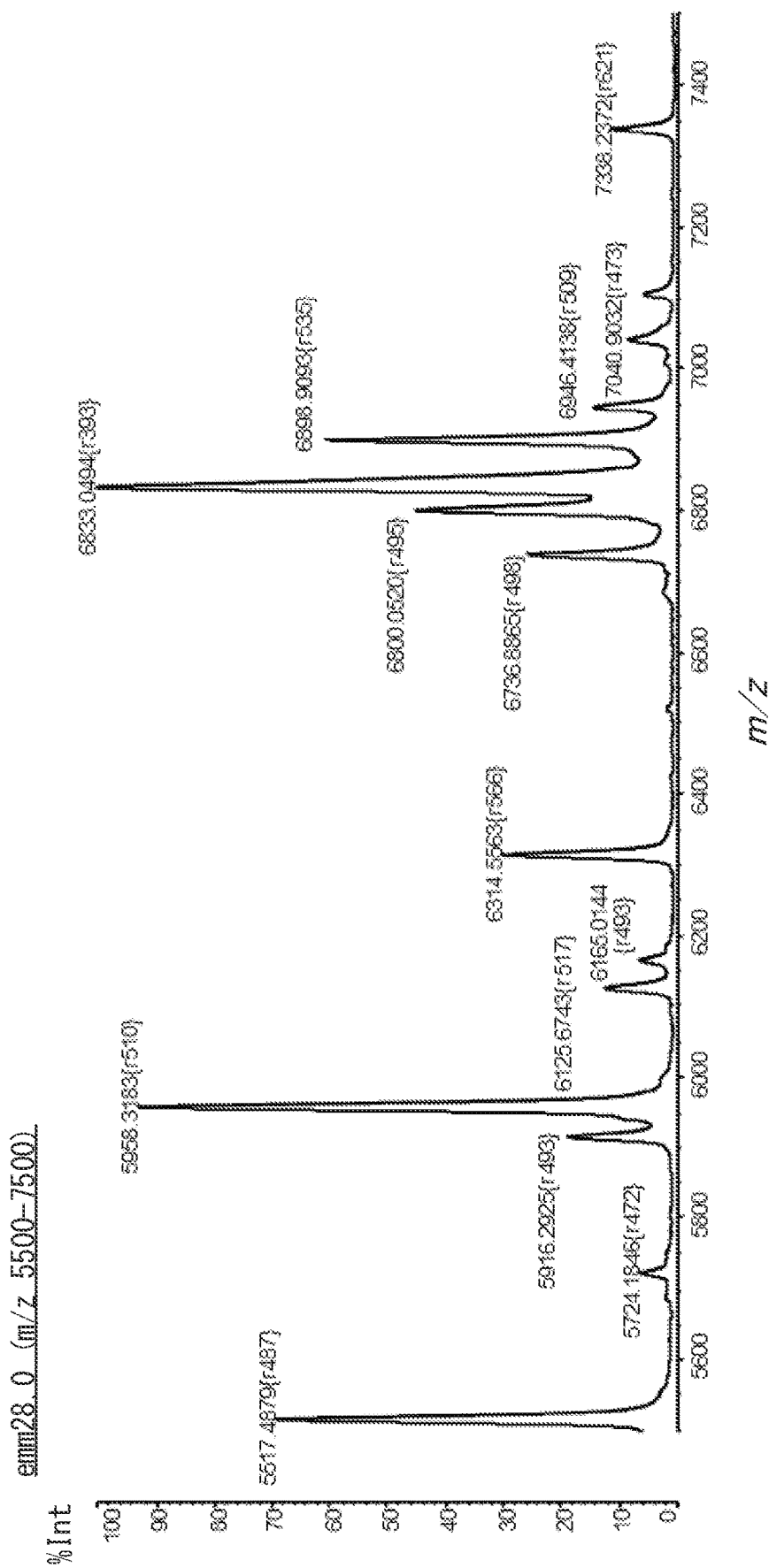
FIG. 9 is a mass spectrum in the m/z range of 5500 to 7500 obtained by mass spectrometry of microorganisms of emm type 28.
Figure 10:
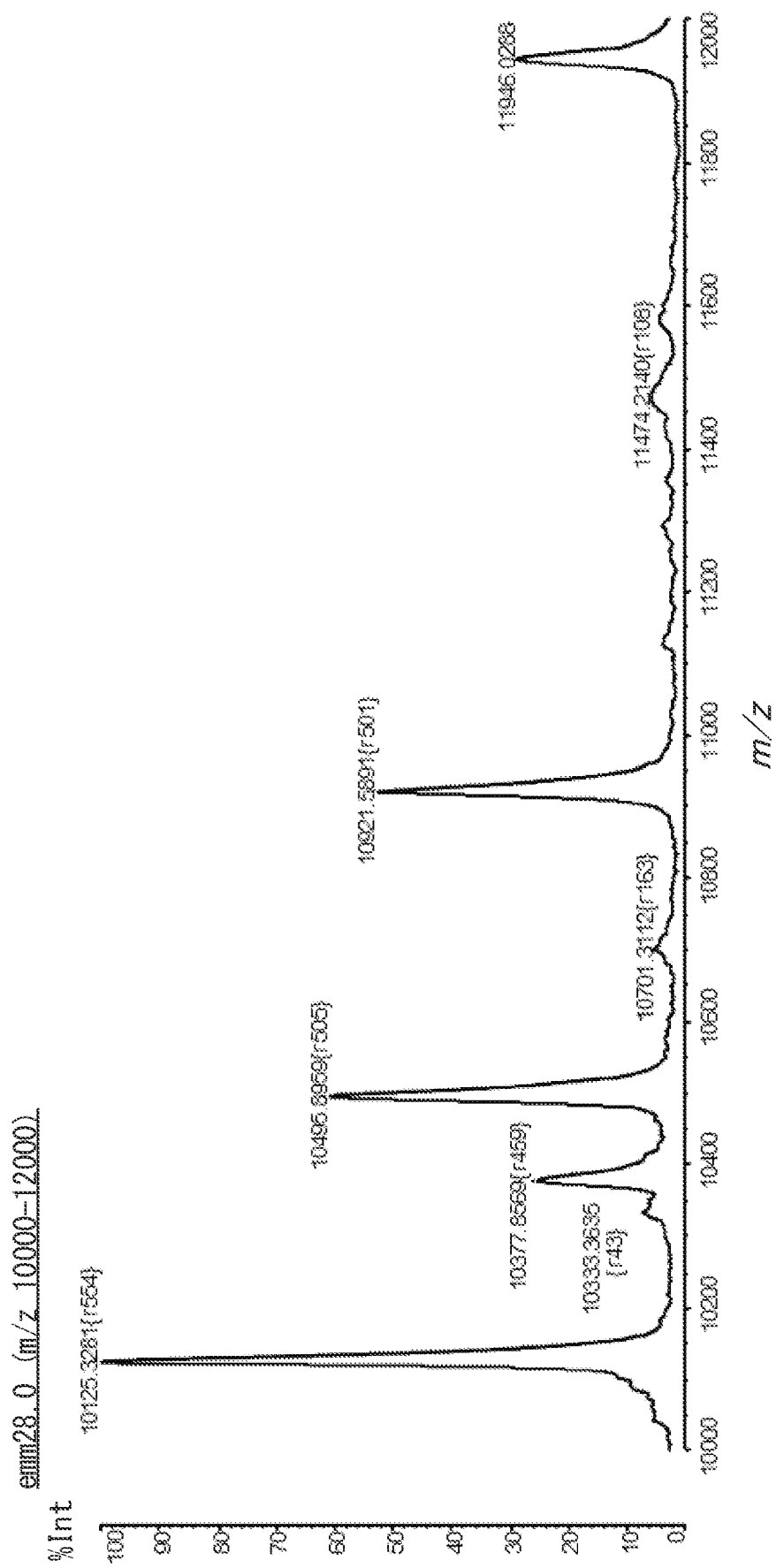
FIG. 10 is a mass spectrum in the m/z range of 10000 to 12000 obtained by mass spectrometry of microorganisms of emm type 28.

FIGS. 8, 9, and 10 are mass spectra of the sample prepared from microorganisms of emm type 28 (emm 28.0) in the m/z ranges of 2000 to 20000, 5500 to 7500, and 10000 to 12000, respectively.

Figure 11:
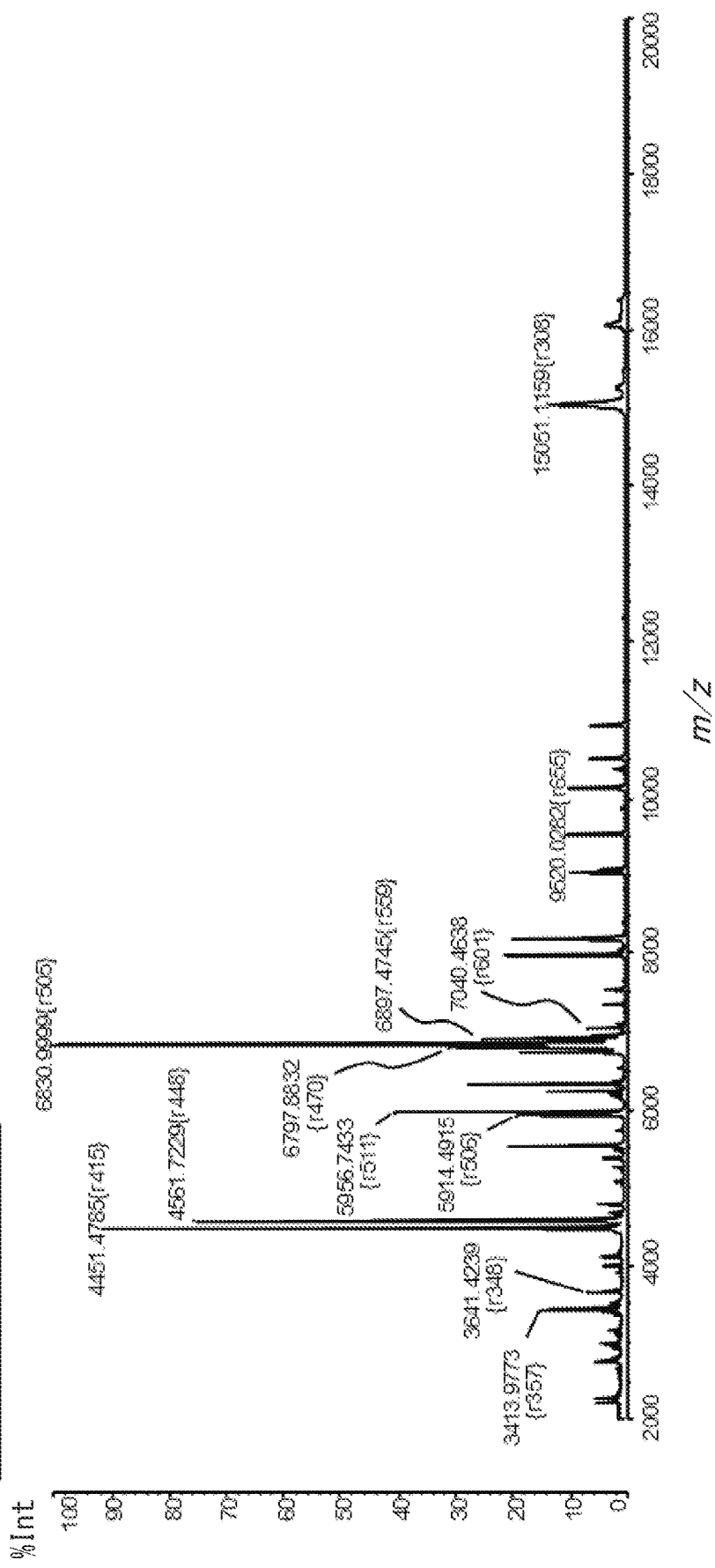
FIG. 11 is a mass spectrum in the m/z range of 2000 to 20000 obtained by mass spectrometry of microorganisms of emm type 89.
Figure 12:
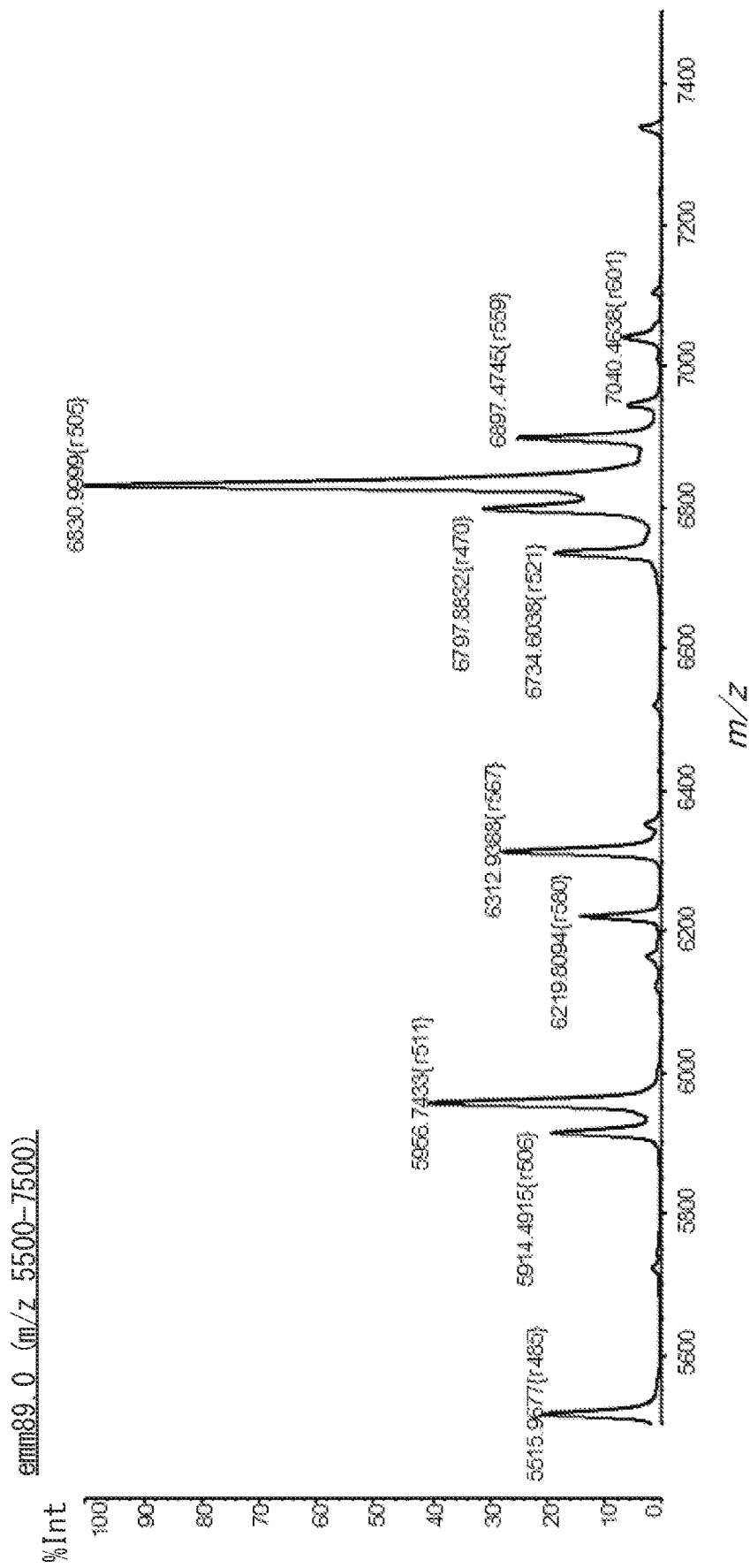
FIG. 12 is a mass spectrum in the m/z range of 5500 to 7500 obtained by mass spectrometry of microorganisms of emm type 89.
Figure 13:
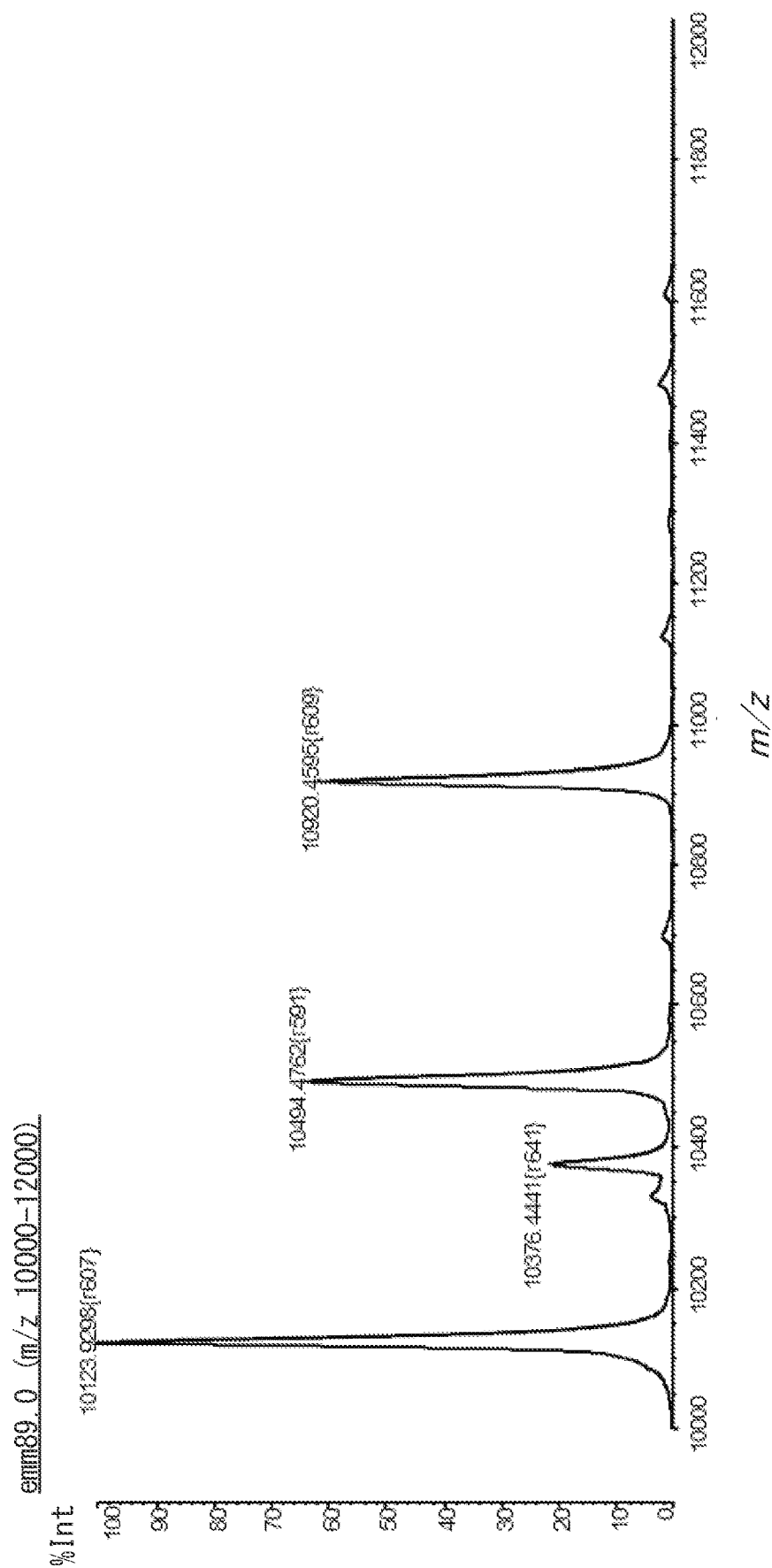
FIG. 13 is a mass spectrum in the m/z range of 10000 to 12000 obtained by mass spectrometry of microorganisms of emm type 89.

FIGS. 11, 12, and 13 are mass spectra of the sample prepared from microorganisms of emm type 89 (emm 89.0) in the m/z ranges of 2000 to 20000, 5500 to 7500, and 10000 to 12000, respectively.

As can be seen from FIGS. 2 to 13, in the mass spectra of the sample prepared from GAS of emm type 1, specific peaks were observed in the first ranges, and in the mass spectra of the sample prepared from GAS of emm type 12, specific peaks were observed in the second ranges.

The disclosure of the following priority application is herein incorporated by reference: Japanese Patent Application No. 2018-185630 filed Sep. 28, 2018

The invention claimed is:
1. An analysis method comprising:
   generating data corresponding to a mass spectrum obtained by subjecting a sample containing a microorganism to mass spectrometry;
   generating information on Group A *Streptococcus* of emm type 1, based on a presence or or magnitude of a peak in a first range of m/z of 10934 or more to 10945 or less in the mass spectrum; and
   identifying whether or not the microorganism is Group A *Streptococcus* of emm type 1, based on the presence or magnitude of the peak in the first range.
2. The analysis method according to claim 1, wherein in the mass spectrometry, the sample is ionized by matrix-assisted laser desorption/ionization, using sinapic acid or CHCA as a matrix.
3. An analysis method comprising:
   generating data corresponding to a mass spectrum obtained by subjecting a sample containing a microorganism to mass spectrometry;
   generating information on Group A *Streptococcus* of emm type 12 based on a presence or absence, or magnitude of a peak in a second range of m/z of 6908 or more to 6918 or less in the mass spectrum; and
   identifying whether or not the microorganism is Group A *Streptococcus* of emm type 12, based on the presence or absence, or magnitude of a peak in the second range.
4. The analysis method according to claim 3, wherein in the mass spectrometry, the sample is ionized by matrix-assisted laser desorption/ionization, using sinapic acid or CHCA as a matrix.

* * * * *